(12) United States Patent
Weiskopf et al.

(10) Patent No.: US 7,381,845 B2
(45) Date of Patent: Jun. 3, 2008

(54) NITRILE HYDROGENATION ON HETEROGENEOUS CATALYSTS IN THE PRESENCE OF IONIC LIQUIDS

(75) Inventors: Verena Weiskopf, Alsheim (DE); Till Gerlach, Ludwigshafen (DE); Kirsten Wenz, Mannheim (DE)

(73) Assignee: BASF Aktiengesellschaft (DE)

( * ) Notice: Subject to any disclaimer, the term of this patent is extended or adjusted under 35 U.S.C. 154(b) by 101 days.

(21) Appl. No.: 10/583,726

(22) PCT Filed: Dec. 20, 2004

(86) PCT No.: PCT/EP2004/014495

§ 371 (c)(1),
(2), (4) Date: Jun. 20, 2006

(87) PCT Pub. No.: WO2005/061429

PCT Pub. Date: Jul. 7, 2005

(65) Prior Publication Data

US 2007/0142673 A1    Jun. 21, 2007

(30) Foreign Application Priority Data

Dec. 22, 2003  (DE) ................................ 103 61 071

(51) Int. Cl.
*C07C 209/48* (2006.01)
(52) U.S. Cl. .................. 564/490; 564/415; 564/491; 564/492; 564/493
(58) Field of Classification Search .................. None
See application file for complete search history.

(56) References Cited

U.S. PATENT DOCUMENTS 3,657,368 A  *  4/1972  Parshall ..................... 585/277
3,919,271 A      11/1975  Parshall

FOREIGN PATENT DOCUMENTS

WO    WO-02/096862 A2    12/2002

OTHER PUBLICATIONS

Miller et al, 1960. "Substitution and Addition Reactions of the Fluoroolefins. IV. Reactions of Fluoride Ion with Fluoroolefins." *Journal of the American Chemical Society* 82, 3091-3099.

* cited by examiner

*Primary Examiner*—Brian Davis
(74) *Attorney, Agent, or Firm*—Connolly Bove Lodge & Hutz LLP

(57) ABSTRACT

A process for hydrogenating nitrile functions present in organic compounds over at least one heterogeneous catalyst, in which the hydrogenation is carried out in the presence of an ionic liquid, is described.

17 Claims, No Drawings

NITRILE HYDROGENATION ON HETEROGENEOUS CATALYSTS IN THE PRESENCE OF IONIC LIQUIDS

CROSS REFERENCE TO RELATED APPLICATIONS

This application is a National Phase of PCT/EP2004/014495, filed Dec. 20, 2004, which claims priority to German application 103 61 071.5, filed Dec. 22, 2003.

The present invention relates to a process for hydrogenating nitrile functions present in organic compounds over at least one heterogeneous catalyst.

Nitriles, dinitriles or trinitriles are widely used starting materials in the chemical, pharmaceutical and agrochemical industries. Hydrogenation of nitrites or dinitriles makes it possible to obtain amines, aminonitriles or diamines which are used as basic chemicals or additives for polymers, as surface-active substances, chelating agents or generally as intermediates in chemical synthesis.

Homogeneous and heterogeneous processes can be used for the hydrogenation of nitrile functions. Heterogeneous processes are advantageous in industry, since the use of heterogeneous catalysts and the recycling of these catalysts is generally significantly simpler and cheaper than in the case of homogeneous catalysts.

The heterogeneous hydrogenation of nitrites or dinitriles is carried out using catalysts comprising, for example, one or more of the metals nickel, cobalt, copper, palladium, platinum, rhenium, ruthenium and iron. These catalysts for hydrogenating nitrites or dinitriles generally have an unsatisfactory operating life. Furthermore, the selectivity in hydrogenations of nitriles to primary, secondary or tertiary amines is unsatisfactory: thus, for example, when the preparation of primary amines is desired, the unwanted, more highly substituted amines are frequently also formed. In the hydrogenation of dinitriles, it is also frequently not possible to obtain the intermediate aminonitrile at high conversions of the dinitrile and at the same time high selectivities.

Higher operating lives and improved selectivities in the hydrogenation of nitrites can be achieved by carrying out the hydrogenation at a high pressure and high temperature in the presence of excess ammonia. Furthermore, use is frequently made of a solvent which consists either of a reactant (e.g. nitrile or amine) or customary solvents (e.g. organic solvents or water).

If ammonia or conventional solvents are used in the known processes for hydrogenating nitrites in order to avoid the abovementioned disadvantages, not only an elevated pressure during the reaction but also a complicated work-up for the recirculation of ammonia or the conventional solvent are generally necessary.

A further possible way of improving the selectivity in processes for the hydrogenation of nitrites is the use of additives. Additives used are alkali metal hydroxides or the like with or without water and also, for example, tetraalkylammonium or tetraalkylphosphonium salts having hydroxides, azides, fluorides, thiocyanides or cyanates as counterions. The salts which are obtained as solids or in solution under the prevailing reaction conditions of the heterogeneous hydrogenation of nitrites are generally not recycled in the known processes, but instead have to be disposed of in an environmentally acceptable manner and thus make the process more expensive.

U.S. Pat. No. 3,919,271 describes the hydrogenation of nitrites in the presence of dispersions of a metal halide in ammonium or phosphonium stannates or germanates. The dispersions used only in catalytic amounts are not recovered. However, the use of these salts which have a melting point above 100° C. restricts the temperatures which can be employed and restricts control of the polarities of the mixture to be hydrogenated. In addition, stannates and germanates are undesirable on an industrial scale because of their toxicity and the problems associated with disposal of waste.

An increase in selectivity of nitrile hydrogenation can also be achieved by addition of acid. This allows, apart from a possible positive alteration in the active centers of the catalyst, removal of the amine formed via the ammonium salt. However, a problem is that a salt from which the amine has to be liberated by means of alkalis is formed, so that this process is made more expensive by the necessity of solids handling.

It is therefore an object of the present invention to provide a process for hydrogenating nitrile functions over at least one heterogeneous catalyst, which substantially avoids the above-described disadvantages. In this process, a lower molar ratio of ammonia to nitrile should preferably be necessary to achieve the same or improved selectivity and operating life than in the known processes. The process should particularly preferably make it possible to dispense with the use of ammonia completely. A further object of the present invention is to provide a process for hydrogenating nitrile functions over at least one heterogeneous catalyst, in which the total pressure necessary for a satisfactory selectivity and operating life is preferably reduced compared to the known processes. The abovementioned objects should be obtained with very little occurrence of waste and a simple and therefore economical work-up of the various products or recirculated materials.

The solution of this object starts out from a process for hydrogenating nitrile functions present in organic compounds over at least one heterogeneous catalyst. In the process of the invention, the hydrogenation is carried out in the presence of an ionic liquid.

The ionic liquid can function as solvent.

It is, for example, possible to use the ionic liquid as sole solvent, i.e. in a large excess over starting material and product, in the process of the invention.

However, it is also possible to use the ionic liquid in combination with another, conventional solvent. Any ratio of ionic liquid to solvent can be employed in this case. However, particular preference is given to ratios of from 1 to 99% by volume, in particular from 1 to 50% by volume, especially from 1 to 25% by volume, of ionic liquid in the conventional solvent, in each case based on the total reaction mixture.

The conventional solvent can have the same polarity, a similar polarity or a complementary polarity as/to the ionic liquid. Furthermore, the conventional solvent can be miscible or immiscible with the ionic liquid or form stable or unstable emulsions with the ionic liquid.

It is also possible to use the starting material, i.e. the nitrile to be hydrogenated, and/or the product, i.e. the amine or aminonitrile to be prepared, as conventional solvent, with or without an additional conventional solvent.

Suitable conventional solvents are polar solvents selected from the group consisting of methanol, ethanol, higher alcohols, polyols, pyridine, quinoline, dichloromethane, chloroform, alkyl nitrites such as acetonitrile, pentenenitrile isomers, adiponitrile, dimethylformamide, dimethyl sulfoxide, water, acetone, higher ketones, tetrahydrofuran, 1,4-dioxane, vinylpyrrolidone, N-methylpyrrolidone, esters, for example ethyl acetate, acids, for example acetic acid, propionic acid or adipic acid, amines or diamines, for example hexamethylenediamine, aminocapronitrile, trialkylamines, and short-chain ethers, for example diethyl ether. Suitable nonpolar solvents are preferably selected from the group consisting of hydrocarbons, aromatics, for example toluene, xylene, mesitylene, and oligomeric or polymeric ethers.

It is also conceivable for the ionic liquid to be used as additive in the process of the invention for the hydrogenation of nitriles. The content of ionic liquid is preferably from 0.0001 to 10% by volume, particularly preferably from 0.001 to 5% by volume, in each case based on the total reaction mixture.

In the process of the invention, preference is given to the ionic liquid being present in the liquid state during the hydrogenation. This dispenses with costly and complicated solids handling.

The ratio of nitrile or dinitrile to be hydrogenated to ionic liquid and thus the precise composition of the reaction mixture is dependent on the nitrile or the amine formed and on the reaction conditions chosen. The ratio is preferably set so that both a very high yield and a very high selectivity are achieved. To achieve this, the amount of hydrogen introduced has to be sufficient to hydrogenate at least part of the nitrile. Precise pressure and temperature conditions are set as a function of the reactants used and the reaction conditions chosen.

Ionic Liquid

Ionic liquids are, according to the definition of Wasserscheid and Keim in "Angewandte Chemie" 2000, 112, pages 3926-3945, salts which melt at relatively low temperatures and have a nonmolecular, ionic character. They are liquid even at relatively low temperatures and when molten have a relatively low viscosity. They have very good solvent capabilities for a large number of organic, inorganic and polymeric substances. In addition, they are generally nonflammable and have no measurable vapor pressure.

Ionic liquids are made up of positive and negative ions, but are electrically neutral overall. Both the positive ions and the negative ions are predominantly monovalent, but multivalent anions and/or cations, for example ones having from one to five, preferably from one to four, particularly preferably from one to three, in particular one or two, electrical charges per ion are also possible. The charges can be present in various localized or delocalized regions within a molecule, i.e. in a betaine-like fashion, or can be present on separate anions and cations. Preference is given to ionic liquids which are made up of at least one cation and at least one anion.

The present invention is not restricted to specific ionic liquids; it is possible to use all suitable ionic liquids, including mixtures of various ionic liquids, for example, inter alia, mixtures of conventional solid, gaseous or liquid entrainers for concentrating a component of a mixture, e.g. N-methylpyrrolidone, dimethylformamide, ethanediol, benzene, cyclohexane, water, etc., with ionic liquids.

Preference is given to ionic liquids having a very low melting point, particularly preferably below 200° C., in particular below 100° C., especially below 76° C.

The ionic liquids have a molar mass of preferably not more than 1000 g/mol, particularly preferably not more than 500 g/mol.

Preferred cations are ammonium or phosphonium ions or cations containing at least one five- or six-membered heterocycle which contains at least one phosphorus or nitrogen atom and optionally an oxygen or sulfur atom. Preference is given to cations containing at least one five- or six-membered heterocycle which contains one, two or three nitrogen atoms and one sulfur or one oxygen atom. Very particular preference is given to cations which contain at least one five- or six-membered heterocycle containing one or two nitrogen atoms.

Furthermore, preference is given to cations selected from among the compounds of the formulae (Ia) to (Iw),

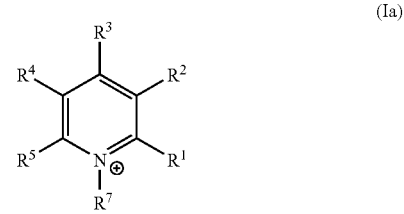

(Ia)

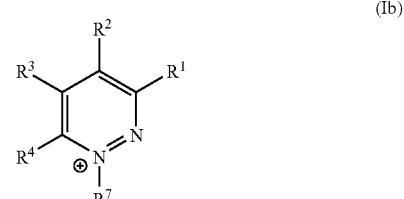

(Ib)

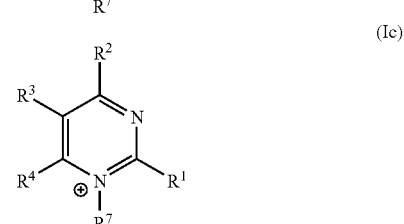

(Ic)

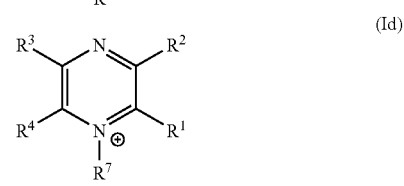

(Id)

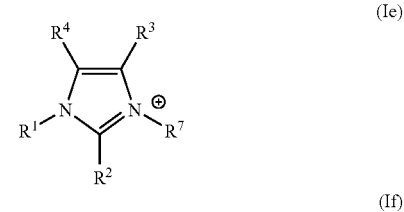

(Ie)

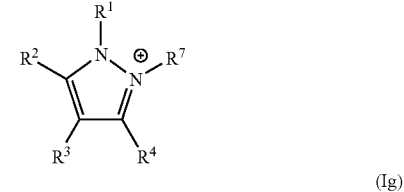

(If)

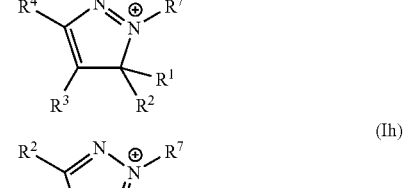

(Ig)

(Ih)

-continued

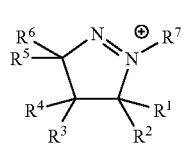 (Ii)

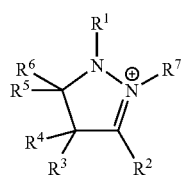 (Ij)

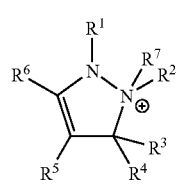 (Ik)

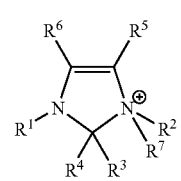 (Il)

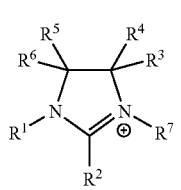 (Im)

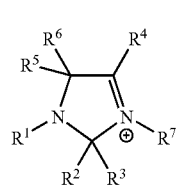 (In)

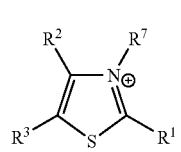 (Io)

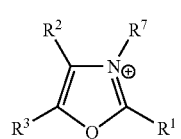 (Ip)

-continued

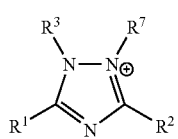 (Iq)

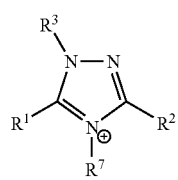 (Ir)

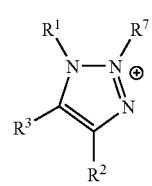 (Is)

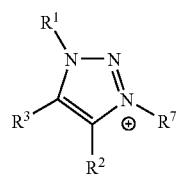 (It)

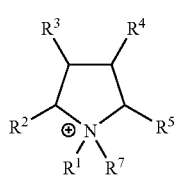 (Iu)

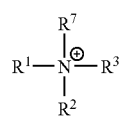 (Iv)

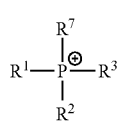 (Iw)

and also oligomers or polymers in which these structures are present, where the radicals $R^1$, $R^2$, $R^3$, $R^4$, $R^5$, $R^6$ and $R^7$ are each, independently of one another, hydrogen or $C_1$-$C_{18}$-alkyl, $C_2$-$C_{18}$-akyl which may be interrupted by one or more nonadjacent oxygen and/or sulfur atoms and/or one or more substituted or unsubstituted imino groups, $C_6$-$C_{12}$-aryl, $C_5$-$C_{12}$-cycloalkyl or a five- or six-membered, oxygen-, nitrogen- and/or sulfur-containing heterocycle, each of which may be unsubstituted or bear functional groups, aryl, alkyl, aryloxy, alkyloxy, halogen, heteroatoms and/or heterocycles as substituents, or two of the radicals together form an unsaturated, saturated or aromatic ring which may be interrupted by one or more oxygen and/or sulfur atoms and/or one or more substituted or unsubstituted imino groups, where the radicals may each be substituted by functional groups, aryl, alkyl, aryloxy, alkyloxy, halogen, heteroatoms and/or heterocycles.

$R^7$ can also be $C_1$-$C_{18}$-alkyloyl (alkylcarbonyl), $C_1$-$C_{18}$-alkyloxycarbonyl, $C_5$-$C_{12}$-cycloalkylcarbonyl or $C_6$-$C_{12}$-aryloyl (arylcarbonyl), where the radicals mentioned may each be substituted by functional groups, aryl, alkyl, aryloxy, alkyloxy, halogen, heteroatoms and/or heterocycles, with the $C_1$-$C_{18}$ referring to alkyl.

In these definitions, $C_1$-$C_{18}$-alkyl which may be unsubstituted or bear functional groups, aryl, alkyl, aryloxy, alkyloxy, halogen, heteroatoms and/or heterocycles as substituents is, for example, methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, heptadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonylethyl, 2-ethoxycarbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxyethyl, 2-hydroxypropyl, 3-hydroxypropyl, 4-hydroxybutyl, 6-hydroxyhexyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethyl-aminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl, and $C_2$-$C_{18}$-alkyl which may be interrupted by one or more nonadjacent oxygen and/or sulfur atoms and/or one or more substituted or unsubstituted imino groups is, for example, 5-hydroxy-3-oxapentyl, 8-hydroxy-3,6-dioxaoctyl, 11-hydroxy-3,6,9-trioxa-undecyl, 7-hydroxy-4-oxaheptyl, 11-hydroxy-4,8-dioxaundecyl, 15-hydroxy-4,8,12-trioxa-pentadecyl, 9-Hydroxy-5-oxa-nonyl, 14-Hydroxy-5,10-oxatetradecyl, 5-Methoxy-3-oxapentyl, 8-methoxy-3,6-dioxaoctyl, 11-methoxy-3,6,9-trioxaundecyl, 7-methoxy-4-oxaheptyl, 11-methoxy-4,8-dioxaundecyl, 15-methoxy-4,8,12-trioxapentadecyl, 9-methoxy-5-oxanonyl, 14-methoxy-5,10-oxatetradecyl, 5-ethoxy-3-oxapentyl, 8-ethoxy-3,6-dioxaoctyl, 11-ethoxy-3,6,9-trioxaundecyl, 7-ethoxy-4-oxaheptyl, 11-ethoxy-4,8-dioxaundecyl, 15-ethoxy-4,8,12-trioxapentadecyl, 9-ethoxy-5-oxanonyl or 14-ethoxy-5,10-oxatetradecyl.

If two radicals form a ring, these radicals can together form 1,3-propylene, 1,4-butylene, 2-oxa-1,3-propylene, 1-oxa-1,3-propylene, 2-oxa-1,3-propylene, 1-oxa-1,3-propenylene, 1-aza-1,3-propenylene, 1-$C_1$-$C_4$-alkyl-1-aza-1,3-propenylene, 1,4-buta-1,3-dienylene, 1-aza-1,4-buta-1,3-dienylene or 2-aza-1,4-buta-1,3-dienylene.

The number of oxygen and/or sulfur atoms and/or imino groups in the ionic liquid is not subject to any restrictions. In general, it is not more than 5 per radical, preferably not more than 4, in particular not more than 3.

Furthermore, at least one carbon atom, particularly preferably at least two carbon atoms, is/are located between two heteroatoms.

Substituted and unsubstituted imino groups can be, for example, imino, methylimino, isopropylimino, n-butylimino or tert-butylimino.

Furthermore, functional groups are carboxy, carboxamide, hydroxy, di($C_1$-$C_4$-alkyl)amino, $C_1$-$C_4$-alkyloxycarbonyl, cyano or $C_1$-$C_4$-alkyloxy, $C_6$-$C_{12}$-aryl which may be unsubstituted or bear functional groups, aryl, alkyl, aryloxy, alkyloxy, halogen, heteroatoms and/or heterocycles as substituents is, for example, phenyl, tolyl, xylyl, α-naphthyl, β-naphthyl, 4-diphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-tri-methylphenyl, 2,6-diethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxyethylphenyl, $C_5$-$C_{12}$-cycloalkyl which may be unsubstituted or bear functional groups, aryl, alkyl, aryloxy, alkyloxy, halogen, heteroatoms and/or heterocycles as substituents is, for example, cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl or a saturated or unsaturated bicyclic system such as norbornyl or norborneneyl, a five- or six-membered, oxygen-, nitrogen- and/or sulfur-containing heterocycle is, for example, furyl, thienyl, pyrryl, pyridyl, indolyl, benzoxazolyl, dioxolyl, dioxyl, benzimidazolyl, benzothiazolyl, dimethylpyridyl, methylquinolyl, dimethylpyrryl, methoxyfuryl, dimethoxypyridyl, difluoropyridyl, methylthienyl, isopropylthienyl or tert-butylthienyl and $C_1$-$C_4$-alkyl is, for example, methyl, ethyl, propyl, isopropyl, n-butyl, sec-butyl or tert-butyl.

$C_1$-$C_{18}$-alkyloyl (alkylcarbonyl) can be, for example, acetyl, propionyl, n-butyloyl, sec-butyloyl, tert-butyloyl, 2-etylhexylcarbonyl, decanoyl, dodecanoyl, chloroacetyl, trichloroacetyl or trifluoroacetyl.

$C_1$-$C_{18}$-alkyloxycarbonyl can be, for example, methyloxycarbonyl, ethyloxycarbonyl, propyloxycarbonyl, isopropyloxycarbonyl, n-butyloxycarbonyl, sec-butyloxycarbonyl, tert-butyloxycarbonyl, hexyloxycarbonyl, 2-ethylhexyloxycarbonyl or benzyloxycarbonyl.

$C_5$-$C_{12}$-cycloalkylcarbonyl can be, for example, cyclopentylcarbonyl, cyclohexyl-carbonyl or cyclododecylcarbonyl.

$C_6$-$C_{12}$-aryloyl (arylcarbonyl) can be, for example, benzoyl, toluyl, xyloyl, α-naphthoyl, β-naphthoyl, chlorobenzoyl, dichlorobenzoyl, trichlorobenzoyl or trimethylbenzoyl.

Preference is given to $R^1$, $R^2$, $R^3$, $R^4$, $R^5$ and $R^6$ each being, independently of one another, hydrogen, methyl, ethyl, n-butyl, 2-hydroxyethyl, 2-cyanoethyl, 2-(methoxycarbonyl)ethyl, 2-(ethoxycarbonyl)ethyl, 2-(n-butoxycarbonyl)ethyl, dimethylamino, diethylamino or chlorine.

$R^7$ is preferably methyl, ethyl, n-butyl, 2-hydroxyethyl, 2-cyanoethyl, 2-(methoxy-carbonyl)ethyl, 2-(ethoxycarbonyl)ethyl, 2-(n-butoxycarbonyl)ethyl, acetyl, propionyl, t-butyryl, methoxycarbonyl, ethoxycarbonyl or n-butoxycarbonyl.

Particularly preferred pyridinium ions (Ia) are those in which one of the radicals $R^1$ to $R^5$ is methyl, ethyl or chlorine, $R^7$ is acetyl, methyl, ethyl or n-butyl and all other radicals are hydrogen, or $R^3$ is dimethylamino, $R^7$ is acetyl, methyl, ethyl or n-butyl and all other radicals are hydrogen or $R^7$ is acetyl, methyl, ethyl or n-butyl and all other radicals are hydrogen or $R^2$ is carboxy or carboxamide, $R^7$ is acetyl, methyl, ethyl or n-butyl and all other radicals are hydrogen or $R^1$ and $R^2$ or $R^2$ and $R^3$ are together 1,4-buta-1,3-dienylene, $R^7$ is acetyl, methyl, ethyl or n-butyl and all other radicals are hydrogen.

Particularly preferred pyridazinium ions (Ib) are those in which one of the radicals $R^1$ to $R^4$ is methyl or ethyl, $R^7$ is acetyl, methyl, ethyl or n-butyl and all other radicals are hydrogen or $R^7$ is acetyl, methyl, ethyl or n-butyl, and all other radicals are hydrogen.

Particularly preferred pyrimidinium ions (Ic) are those in which $R^2$ to $R^4$ are each hydrogen or methyl, $R^7$ is acetyl, methyl, ethyl or n-butyl and $R^1$ is hydrogen, methyl or ethyl, or $R^2$ and $R^4$ are each methyl, $R^3$ is hydrogen and $R^1$ is hydrogen, methyl or ethyl and $R^7$ is acetyl, methyl, ethyl or n-butyl.

Particularly preferred pyrazinium ions (Id) are those in which $R^2$ to $R^4$ are all methyl and $R^7$ is acetyl, methyl, ethyl or n-butyl or $R^7$ is acetyl, methyl, ethyl or n-butyl and all other radicals are hydrogen.

Particularly preferred imidazolium ions (Ie) are those in which, independently of one another,
$R^1$ is selected from the group consisting of methyl, ethyl, n-propyl, n-butyl, n-pentyl, n-octyl, n-decyl, n-dodecyl, 2-hydroxyethyl and 2-cyanoethyl,
$R^7$ is acetyl, methyl, ethyl or n-butyl and
$R^2$ to $R^4$ are each, independently of one another, hydrogen, methyl or ethyl.

Particularly preferred 1H-pyrazolium ions (If) are those in which, independently of one another,
$R^1$ is selected from among hydrogen, methyl and ethyl,
$R^2$, $R^3$ and $R^4$ are selected from among hydrogen and methyl and
$R^7$ is selected from among acetyl, methyl, ethyl and n-butyl.

Particularly preferred 3H-pyrazolium ions (Ig) are those in which, independently of one another,
$R^1$ is selected from among hydrogen, methyl and ethyl,
$R^2$, $R^3$ and $R^4$ are selected from among hydrogen and methyl and
$R^7$ is selected from among acetyl, methyl, ethyl and n-butyl.

Particularly preferred 4H-pyrazolium ions (Ih) are those in which, independently of one another,
$R^1$ to $R^4$ are selected from among hydrogen and methyl and
$R^7$ is selected from among acetyl, methyl, ethyl and n-butyl.

Particularly preferred 1-pyrazolinium ions (Ii) are those in which, independently of one another,
$R^1$ to $R^6$ are selected from among hydrogen and methyl and
$R^7$ is selected from among acetyl, methyl, ethyl and n-butyl.

Particularly preferred 2-pyrazolinium ions (Ij) are those in which, independently of one another,
$R^1$ is selected from among hydrogen, methyl, ethyl and phenyl,
$R^7$ is selected from among acetyl, methyl, ethyl and n-butyl and
$R^2$ to $R^6$ are selected from among hydrogen and methyl.

Particularly preferred 3-pyrazolinium ions (Ik) are those in which, independently of one another,
$R^1$ and $R^2$ are selected from among hydrogen, methyl, ethyl and phenyl,
$R^7$ is selected from among acetyl, methyl, ethyl and n-butyl and
$R^3$ to $R^6$ are selected from among hydrogen and methyl.

Particularly preferred imidazolinium ions (Il) are those in which, independently of one another,
$R^1$ and $R^2$ are selected from among hydrogen, methyl, ethyl, n-butyl and phenyl,
$R^7$ is selected from among acetyl, methyl, ethyl and n-butyl and
$R^3$ and $R^4$ are selected from among hydrogen, methyl and ethyl and
$R^5$ and $R^6$ are selected from among hydrogen and methyl.

Particularly preferred imidazolinium ions (Im) are those in which, independently of one another,
$R^1$ and $R^2$ are selected from among hydrogen, methyl and ethyl,
$R^7$ is selected from among acetyl, methyl, ethyl and n-butyl and
$R^3$ to $R^6$ are selected from among hydrogen and methyl.

Particularly preferred imidazolinium ions (In) are those in which, independently of one another,
$R^1$, $R^2$ and $R^3$ are selected from among hydrogen, methyl and ethyl,
$R^7$ is selected from among acetyl, methyl, ethyl and n-butyl and
$R^4$ to $R^6$ are selected from among hydrogen and methyl.

Particularly preferred thiazolium ions (Io) or oxazolium ions (Ip) are those in which, independently of one another,
$R^1$, $R^2$ and $R^3$ is selected from among hydrogen, methyl, ethyl and phenyl,
$R^7$ is selected from among acetyl, methyl, ethyl and n-butyl and
$R^2$ and $R^3$ are selected from among hydrogen and methyl.

Particularly preferred 1,2,4-triazolium ions (Iq) and (Ir) are those in which, independently of one another,
$R^1$ and $R^2$ are selected from among hydrogen, methyl, ethyl and phenyl,
$R^7$ is selected from among acetyl, methyl, ethyl and n-butyl and
$R^3$ is selected from among hydrogen, methyl and phenyl.

Particularly preferred 1,2,3-triazolium ions (Is) and (It) are those in which, independently of one another,
$R^1$ is selected from among hydrogen, methyl and ethyl,
$R^7$ is selected from among acetyl, methyl, ethyl and n-butyl and
$R^2$ and $R^3$ are selected from among hydrogen and methyl or
$R^2$ and $R^3$ together form 1,4-buta-1,3-dienylene and all others are hydrogen.

Particularly preferred pyrrolidinium ions (Iu) are those in which, independently of one another,
$R^1$ and $R^7$ are selected from among acetyl, methyl, ethyl and n-butyl and
$R^2$, $R^3$, $R^4$ and $R^5$ are each hydrogen.

Particularly preferred ammonium ions (Iv) are those in which, independently of one another, $R^7$ is selected from among acetyl, methyl, ethyl and n-butyl and $R^1$, $R^2$ and $R^3$ are selected from among methyl, ethyl, n-butyl, 2-hydroxyethyl, benzyl and phenyl.

Particularly preferred phosphonium ions (Iw) are those in which, independently of one another, $R^7$ is selected from among acetyl, methyl, ethyl and n-butyl and $R^1$, $R^2$ and $R^3$ are selected from among phenyl, phenoxy, ethoxy and n-butoxy.

Among the abovementioned ions, preference is given to ammonium, phosphonium, pyridinium and imidazolium ions.

Very particularly preferred cations are 1,2-dimethylpyridinium, 1-methyl-2-ethyl-pyridinium, 1-methyl-2-ethyl-6-methylpyridinium, N-methylpyridinium, 1-butyl-2-methylpyridinium, 1-butyl-2-ethylpyridinium, 1-butyl-2-ethyl-6-methylpyridinium, N-butyl-pyridinium, 1-butyl-4-methylpyridinium, 1,3-dimethylimidazolium, 1,2,3-trimethyl-imidazolium, 1-n-butyl-3-methylimidazolium, 1,3,4,5-tetramethylimidazolium, 1,3,4-trimethylimidazolium, 2,3-dimethylimidazolium, 1-butyl-2,3-dimethylimidazolium, 3,4-dimethylimidazolium, 2-ethyl-3,4-dimethylimidazolium, 3-methyl-2-ethylimidazolium, 3-butyl-1-methylimidazolium, 3-butyl-1-ethylimidazolium, 3-butyl-1,2-dimethyl-imidazolium, 1,3-di-n-butylimidazolium, 3-butyl-1,4,5-trimethylimidazolium, 3-butyl-1,4-dimethylimidazolium, 3-butyl-2-methylimidazolium, 1,3-dibutyl-2-methylimidazolium, 3-butyl-4-methylimidazolium, 3-butyl-2-ethyl-4-methylimidazolium and 3-butyl-2-ethyl-imidazolium, 1-methyl-3-octylimidazolium, 1-decyl-3-methylimidazolium.

Particular preference is given to 1-butyl-4-methylpyridinium, 1-n-butyl-3-methyl-imidazolium and 1-n-butyl-3-ethylimidazolium.

Cations derived from diazabicyclononene or diazabicycloundecene and also their mixtures or derivatives are also possible.

As anions, all anions are in principle conceivable.

Preferred anions are halides $F^-$, $Cl^-$, $Br^-$, $I^-$, acetate $CH_3COO^-$, trifluoroacetate CF triflate $CF_3SO_3^-$, sulfate $SO_4^{2-}$, hydrogensulfate $HSO_4^-$, methylsulfate $CH_3OSO_3^-$, ethylsulfate $C_2H_5OSO_3^-$, sulfite $SO_3^{2-}$, hydrogensulfite $HSO_3^-$, chloroaluminates $AlCl_{4/2}Cl_7^-$, $Al_3Cl_{10}^-$, tetrabromoaluminate $AlBr_4^-$, nitrite $NO_2^-$, nitrate $NO_3^-$, dichlorocuprate $CuCl_2^-$, phosphates, phosphate $PO_4^{3-}$, hydrogenphosphate $HPO_4^{2-}$, dihydrogenphosphate $H_2PO_4^-$, carbonate $CO_3^{2-}$, hydrogencarbonate $HCO_3^-$, sulfonate $—SO_3^-$, tosylate p-$CH_3C_6H_4SO_3^-$ and bis(trifluoromethylsulfonyl)imide ($CF_3SO_2$ Heterogeneous Catalyst The heterogeneous catalyst used in the process of the invention can contain a support material or be used as an all-active catalyst. Furthermore, the heterogeneous catalyst can be in the form of powder (suspension process) or in the form of shaped bodies (fixed bed). Typical shaped bodies are spheres, extrudates, hollow extrudates, star extrudates, pellets, crushed material, etc., having characteristic diameters of from 0.5 to 5 mm or else monoliths and similar structured packing (e.g. *Ullmann's Encyclopedia, Sixth Edition,* 2000 *Electronic Release, Chapter Fixed-Bed Reactors, Par. 2: Catalyst Forms for Fixed-Bed Reactors*).

The present invention is not restricted to specific heterogeneous catalysts; it is possible to use all suitable heterogeneous catalysts. Suitable catalysts comprise, for example, metals selected from the group consisting of nickel, cobalt, copper, iron, ruthenium, rhodium, iridium, palladium and platinum. The abovementioned metal catalysts can, if appropriate, also be in the form of skeletal catalysts. The heterogeneous catalysts can be doped or undoped. Suitable dopant metals can be selected from among the elements of groups 3 to 12 of the Periodic Table of the Elements according to the IUPAC nomenclature (Handbook of Chemistry and Physics, 80th edition, 1999-2000).

Furthermore, it is also possible to use combinations of the abovementioned metals as heterogeneous catalysts.

When a supported heterogeneous catalyst is used in the process of the invention, the present invention is not restricted to specific support materials. For example, it is possible to use carbon black, acetylene black, charcoal, graphite, $SiO_2$, $Al_2O_3$, $ZrO_2$, $ZnO_2$, $TiO_2$, MgO, zeolites, hydrotalcites or further support materials known to those skilled in the art in their various possible modifications. The support materials can be additionally doped with, for example, alkali metals or alkaline earth metals or else with phosphorus, halide and/or sulfate salts. In general, the acid/base properties are modified by means of such doping, which can exert a positive influence on the catalytic properties. The abovementioned hydrogenation-active metals can be applied to the support by any suitable method, for example by impregnation, ion exchange, coprecipitation, e.g. precipitation together with the support, precipitation onto a preformed support, ion exchange, chemical vapor deposition (CVD), etc.

When a supported heterogeneous catalyst is used in the process of the invention, the catalytically active metal is present in an amount of preferably from 0.1 to 60% by weight, particularly preferably from 1 to 50% by weight, in particular from 2 to 50% by weight, in each case based on the total catalyst.

If the heterogeneous catalyst is produced in the form of shaped bodies, for instance for a fixed-bed process, it can have any shape. Typical shaped bodies are spheres, extrudates, hollow extrudates, star extrudates, pellets, crushed material, etc., having characteristic diameters of from 0.5 to 5 mm, or else monoliths and similar structured packing (cf. *Ullmann's Encyclopedia, Sixth Edition,* 2000 *Electronic Release, Chapter Fixed-Bed Reactors, Par. 2: Catalyst Forms for Fixed-Bed Reactors*). In a suspension process, the catalyst is used in powder form. Typical particle sizes of such powders are 1-100 μm, but particles significantly smaller than 1 μm can also be used, for instance when carbon black is used as catalyst support. In suspension processes, filtration can be carried out batchwise, for instance by deep-bed filtration. In continuous processes, crossflow filtration is a possibility.

It is in general possible to employ any desired molar ratio of catalyst to nitrile or dinitrile, as long as hydrogenation of the nitrile or dinitrile occurs. The weight ratio of catalyst to nitrile or dinitrile is preferably from 0.0001:1 to 1:1, particularly preferably from 0.001:1 to 0.25:1.

In the process of the invention for hydrogenating nitriles, the heterogeneous catalyst is used in combination with an ionic liquid. It is preferred that the polarity of the heterogeneous catalyst and the polarity of the ionic liquid are matched to one another. For the definition of polarities of ionic liquids, reference may be made to: P. Wasserscheid, T. Welton (editors), Ionic Liquids in Synthesis, Wiley VCH, Weinheim 2003, page 94 ff.

Thus, in the case of a heterogeneous catalyst having a polar surface, a nonpolar ionic liquid is preferred, and in the case of a heterogeneous catalyst having a nonpolar surface, a polar ionic liquid is preferred. Preference is also given to the ionic liquid and catalyst being chosen so that starting material or product reside in a different phase. It is also preferred that the ionic liquid prevents irreversible occupation of the catalyst.

Accordingly, a heterogeneous catalyst having a nonpolar surface and a polar ionic liquid are used in a first embodiment of the present invention. In this embodiment, the catalyst is essentially not wetted by the ionic liquid.

In a second embodiment of the process of the invention, the surface of the heterogeneous catalyst is polar and is not wetted by the comparatively nonpolar ionic liquid.

As a result of the above-described selection of suitable ionic liquids and suitable heterogeneous catalysts, the process of the invention displays a high selectivity which is achieved, for example, by one of the participating components, for example the hydrogenated amine, being removed from the reactive conditions of the hydrogenation into another phase (including, for example, very small droplets in an emulsion). Further catalytic reaction of the product produced is thus suppressed. The selectivity is thus increased by the physical separation of the participating components.

In a third embodiment of the process of the invention, the surface of the catalyst can be polar and be wetted by the polar ionic liquid, so that a nonpolar starting material or product forms a second phase and can be thus be separated from the active catalyst, which may reduce the formation of by-products.

In a fourth embodiment of the process of the invention, a heterogeneous catalyst having a nonpolar surface and a comparatively nonpolar ionic liquid can be used. In this case, polar starting material or product can form a second phase and thus be separated from the active catalyst.

In a fifth embodiment of the process of the invention, irreversible occupation of the surface of the catalyst by secondary components can be prevented by a reversibly coordinating ionic liquid.

In a sixth embodiment of the process of the invention, an ionic liquid which itself coordinates only weakly can generate a polar, ionic environment and thus prevent occupation of the catalyst surface by secondary components (rinsing effect).

In the ideal case, the ionic liquid, for example, coordinates to the catalyst surface more strongly than does the amine end product and thus displaces the latter, as a result of which secondary reactions are prevented. However, the coordination is similar to or weaker than that of the starting material, so that replacement of the ionic liquid by the starting material is possible and the latter can then be reacted on the catalyst surface.

If the ionic liquid exerts coordination effects, it is advantageous but not absolutely necessary for the catalyst surface to be sufficiently accessible to molecules of the ionic liquid.

Hydrogenation

To carry out the process of the invention, it is advantageous for not only the polarity but also the solubility of the various components in the participating solvents or ionic liquids, the viscosities and densities and the gas fluidities or diffusion rates of the participating gases in the various phases to be taken into account.

The hydrogenation in the process of the invention can be carried out with recirculation or without recirculation (single pass). Furthermore, the hydrogenation can be carried out continuously or batchwise. It can be carried out to full conversion or to partial conversion, for example by premature termination. Backmixing is possible but not absolutely necessary in the process. The process of the invention can be carried out in any suitable apparatus known to those skilled in the art. Examples of suitable apparatuses are tube reactors, bubble columns, autoclaves, pressure-rated stirred vessels or reactor cascades. The hydrogenation can be carried out in a single apparatus or in a plurality of apparatuses connected in series, for example in the downflow mode or the upflow mode.

The pressure at which the process of the invention is carried out is preferably from 1 to 300 bar, particularly preferably from 1 to 200 bar, in particular from 1 to 150 bar. The hydrogenation is preferably carried out at a temperature of at least 20° C., in particular 50° C. The hydrogenation is preferably carried out at a temperature of not more than 250° C., particularly preferably not more than 200° C., in particular not more than 150° C.

The process of the invention is, in a particularly preferred embodiment, suitable for the hydrogenation of nitrile functions in an organic compound having at least two nitrile functions. In this respect, particular mention may be made of the preparation of aminonitriles from dinitriles. An example of this is the hydrogenation of adiponitrile to aminocapronitrile, in which hexamethylenediamine is formed to only a minor extent and the proportion of diamine can be controlled by choice of the reactants and reaction conditions.

In a further particularly preferred embodiment, the process is likewise suitable for the hydrogenation of nitrile functions in labile organic compounds which decompose under normal reaction conditions, e.g. in the presence of the hydrogenation product. An example is the hydrogenation of iminodiacetonitrile to diethylenetriamine, in which diethylenetriamine can be produced with high selectivity.

It is possible to carry out the process of the invention in the presence of ammonia, for example at a molar ratio of ammonia to nitrile of from 10 to 1, in particular from 2 to 1. However, in a particularly preferred embodiment of the process of the invention, the hydrogenation takes place in the absence of ammonia.

Any hydrogen-containing fluid can be used for the hydrogenation, as long as the hydrogen content or the after-diffusion of hydrogen in the fluid is sufficient to hydrogenate nitrile functions. The reaction time for the hydrogenation is dependent on the substrate to be hydrogenated, the catalyst used and the hydrogenation conditions.

It can be, for example, from a few minutes to some hours. The gas used for the hydrogenation preferably comprises from 1 to 100% by volume, particularly preferably from 50 to 100% by volume, in particular from 90 to 100% by volume, of hydrogen. In a particularly preferred embodiment, pure hydrogen is used.

The molar ratio of hydrogen, if appropriate in the fluid, to nitrile or dinitrile is not critical, as long as sufficient hydrogen to hydrogenate the nitrile functions is present. In general, hydrogen is used in excess.

The work-up of the reaction product mixture from the process of the invention, i.e. the catalyst (in the case of a suspension process), the ionic liquid and the starting materials and products, can be carried out separately for each individual component or jointly dependent on process requirements, e.g. by means of a particularly preferred and simple distillation of the starting materials, desired products and impurities or by-products. A further possible way of carrying out the work-up is extraction of the participants in the reaction to separate them from the ionic liquid. Filtration may also be possible for separating off the catalyst from the ionic liquid and the reaction mixture.

Starting materials and/or products can also be separated from the ionic liquid and/or the catalyst by simple phase separation. If a conventional solvent is used in addition to the ionic liquid, it can be separated from the ionic liquid by, for example, distillation. If the ionic liquid and the conventional solvent are not miscible with one another, simple phase separation of the ionic liquid from the conventional solvent is also possible.

In the case of a suspension process, catalyst and ionic liquid can be recirculated separately or together. In a fixed-bed process, the ionic liquid can be recirculated to the process.

The ionic liquid is preferably circulated. To remove undesirable materials which accumulate in the ionic liquid, part of the ionic liquid can be discharged from the system, preferably as a purge stream, and be replaced by fresh ionic liquid. The amount of purge stream is preferably from 0 to 15% by weight, particularly preferably less than 10% by weight, in particular less than 5% by weight.

Further variants for the work-up of the ionic liquid instead of discharge from the process are, for example:
- liquid-liquid extraction using immiscible solvents, for example water, organic solvents and acids (depending on whether the ionic liquid is water-soluble or water-insoluble),
- recrystallization,
- membrane permeation or filtration and
- stripping with an inert gas, for example nitrogen,
- reaction to dissociate the ionic liquid, distillation or extraction of the components and reformation of the ionic liquid.

In the ideal case, work-up of the ionic liquid is not necessary since the reaction components or the reaction conditions have been matched to one another so that accumulation of reaction components or by-products, which makes work-up necessary, does not occur.

In the process of the invention, nitrile functions present in organic compounds are hydrogenated. The organic compounds preferably contain one, two or three nitrile functions.

Particular preference is given to hydrogenating organic compounds having the following structural units

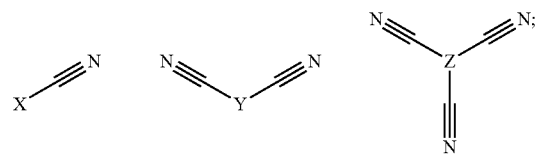

where

X is a linear, branched or cyclic group selected from the group consisting of alkyl, cycloalkyl, alkenyl, alkynyl, aryl, hydroxyalkyl, alkoxyalkyl, aminoalkyl and $C_{1-4}$-aryl, Y and Z are selected from the group consisting of alkyl, cycloalkyl, alkenyl, alkynyl, aryl, alkoxyalkyl and aminoalkyl.

In the process of the invention, particular preference is given to hydrogenating compounds selected from the group consisting of dimethylaminopropionitrile, aminoacetonitrile, formaldehyde cyanohydrin, 3-(2-ethylhexoyl)propionitrile, 3-dimethylaminopropionitrile, methoxypropionitrile and fatty acid nitriles. Particular preference is also given to adiponitrile, iminodiacetonitrile, isophorone nitrilimine, suberonitrile, nitrilotriacetonitrile and isophthalonitrile.

The amines obtained by the process of the invention accordingly have the following structural formulae

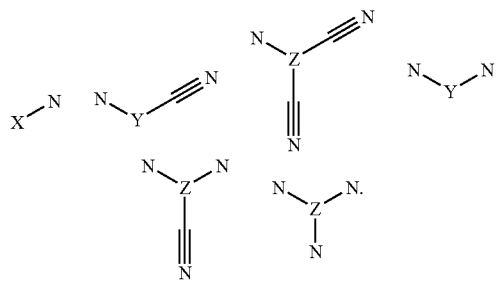

The compounds prepared by the process of the invention are known per se. Particular mention may be made of aminocapronitrile, hexamethylenediamine, diethylenetriamine, ethylenediamine, ethanolamine, aminoacetonitrile, trisamino-ethylamine, dimethylaminopropanamine, methoxypropylamine, 3-(2-ethoxyhexoyl)-propylamine, isophoronediamine, 8-aminooctanitrile, diaminooctane and fatty acid amines.

The preparation of the nitrites used as starting materials in the process of the invention can be carried out by any method known to those skilled in the art. Examples are the Kolbe nitrile synthesis, the Strecker synthesis, heating of acid amides with water-eliminating agents, addition to unsaturated nitrites and heating of aldoximes with acetic anhydride with elimination of water.

The present invention further provides for the use of the above-described ionic liquids in hydrogenations of nitrile functions present in organic compounds over at least one heterogeneous catalyst.

With regard to the organic compounds containing nitrile functions, the ionic liquids and the heterogeneous catalysts, reference may be made to what has been said above.

In addition, the process of the invention has advantages which have not yet been discussed.

The present process provides, for example, the opportunity of separating off products via an acid-base reaction with the acidic ionic liquids. In this case, the desired product is separated off by distillation with shifting of the acid-base equilibria and decomposition of the addition compound of ionic liquid-product. This dispenses with expensive and complicated solids handling due to salt formation and liberation from the solvent.

The process described leads, as mentioned above, to an increase in the selectivity and to an influence on the product ratio between monohydrogenation and dihydrogenation in the case of dinitriles. In addition, the yield of desired product is improved and the life of the catalyst is increased. The ionic liquids can be tailored to requirements over a wide range of polarity, solubility, wetting behavior, melting point, physical and chemical properties by variation of the cations and anions used.

Apart from the increased selectivity, a further significant advantage of the invention is that it proceeds under comparatively low pressure and at low temperatures without addition of ammonia or addition of other additives.

Complicated and expensive waste disposal, e.g. by combustion of additives, can therefore be dispensed with, as can pressure-rated apparatuses and compressors for recirculation of the ammonia used in the known processes. The ionic liquids used can, in contrast to most additives otherwise used, including ammonia, be recirculated simply and economically due to the low vapor pressure.

The process of the invention is illustrated by the following examples.

EXAMPLES

Example 1

In an autoclave, adiponitrile, toluene, ethylimidazolium chloride (weight ratio=1:1:1) and catalyst consisting of Ru/carbon (4.1% by weight) are mixed and reacted at 100° C. and a pressure of 100 bar without addition of ammonia. After 12 hours, the reaction is stopped by cooling, the phases are separated, the catalyst which accumulates primarily at the phase boundary is filtered off and the two phases are analyzed.

Conversion: 60%
Selectivity: 66% in respect of aminocapronitrile, 7% in respect of hexamethylenediamine, ratio of aminocapronitrile to hexamethylenediamine: 5:1.

Example 2

In an autoclave, adiponitrile, toluene, methylimidazolium hydrogensulfate (weight ratio=1:1:1) and catalyst consisting of Ru/carbon (3% by weight) are mixed and reacted at 100° C. and 100 bar without addition of ammonia. After 18 hours, the reaction is stopped by cooling, the phases are separated, the catalyst is filtered off and the two phases are analyzed.

Conversion: 68%
Selectivity: 53% in respect of aminocapronitrile, ratio of aminocapronitrile to hexamethylenediamine: 8:1.

Example 3

In an autoclave, dimethylaminopropionitrile, toluene, ethylimidazolium chloride in a ratio of 1:1:1 and cobalt catalyst (4.1% by weight) are mixed and reacted at 100° C. and a hydrogen pressure of 100 bar without addition of ammonia. After 12 hours, the reaction is stopped by cooling, the phases are separated, the catalyst is filtered off and the two phases are analyzed.

Conversion: 100% Selectivity: 90% in respect of dimethylaminopropylamine

Comparative Example C1

In an autoclave, adiponitrile, toluene (weight ratio=1:1) and catalyst consisting of Ru/carbon (5.6% by weight) are mixed and reacted at 100° C. and 100 bar without addition of ammonia. After 12 hours, the reaction is stopped by cooling and the reaction mixture is analyzed.

Conversion: 100%
Selectivity: 40% in respect of hexamethylenediamine: aminocapronitrile and adipodinitrile are not detectable.

Comparative Example C2

In an autoclave, adiponitrile, toluene (weight ratio=1:1) and catalyst consisting of Ru/carbon (5.6% by weight) are mixed and reacted at 100° C. and 100 bar without addition of ammonia. After 6 hours, a sample is taken and the reaction mixture is analyzed.

Conversion: 69%
Selectivity: 37% in respect of aminocapronitrile; ratio of aminocapronitrile to hexamethylenediamine: 3.2:1.

The invention claimed is:

1. A process for hydrogenating nitrile functions in organic compounds in the presence of at least one heterogeneous catalyst, the process comprising hydrogenating the nitrile function of the organic compound in the presence of an ionic liquid, wherein the ionic liquid comprises an anion selected from the group consisting of halides $F^-$, $Cl^-$, $Br^-$, $I^-$, acetate $CH_3COO^-$, trifluoroacetate $CF_3COO^-$, triflate $CF_3SO_3^-$, sulfate $SO_4^{2-}$, hydrogensulfate $HSO_4^-$, methylsulfate $CH_3OSO_3^-$, ethylsulfate $C_2H_5OSO_3^-$, sulfite $SO_3^{2-}$, hydrogensulfite $HSO_3^-$, chloroaluminates $AlCl_4^-$, $Al_2Cl_7^-$, $Al_3Cl_{10}^-$, tetrabromoaluminate $AlBr_4^-$, nitrite $NO_2^-$, nitrate $NO_3^-$, dichlorocuprate $CuCl_2^-$, phosphates, phosphate $PO_4^{3-}$, hydrogenphosphate $HPO_4^{2-}$, dihydrogenphosphate $H_2PO_4^-$, carbonate $CO_3^{2-}$, hydrogencarbonate $HCO_3^-$, sulfonate $—SO_3^-$, tosylate $p\text{-}CH_3C_6H_4SO_3^-$ and bis(trifluoromethylsulfonyl)imide $(CF_3SO_2)_2N$, and the ionic liquid contains phosphonium ions, or at least one five- or six-membered heterocycle which contains at least one phosphorus or nitrogen atom and optionally, a sulfur atom, an oxygen atom or both oxygen and sulfur atoms, or both the phosphonium ions and the at least one heterocycle.

2. The process according to claim 1, wherein the heterogeneous catalyst comprises a polar surface and the ionic liquid is a nonpolar ionic liquid.

3. The process according to claim 1, wherein the ionic liquid has a melting point below 200° C.

4. The process according to claim 1, wherein the process is conducted in the absence of ammonia.

5. The process according to claim 1, wherein the heterogenous catalyst or the ionic liquid are recirculated separately or together in the process if the process is a suspension process.

6. The process according to claim 1, wherein the heterogeneous catalyst comprises one or more metals selected from the group consisting of nickel, cobalt, copper, iron, ruthenium, rhodium, iridium, palladium and platinum.

7. The process according to claim 1, wherein the hydrogenation is carried out at a temperature of from 20 to 250° C. and/or a pressure of from 1 to 300 bar.

8. The process according to claim 1, wherein the nitriles to be hydrogenated have at least one of the following structural units:

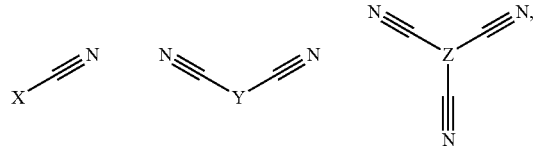

where X in the structural units is a linear, branched or cyclic group selected from the group consisting of alkyl, cycloalkyl, alkenyl, alkynyl, aryl, hydroxyalkyl, alkoxyalkyl, aminoalkyl and $C_{1-4}$-aryl and Y and Z are selected from the group consisting of alkyl, cycloalkyl, alkenyl, alkinyl, aryl, alkoxyalkyl and aminoalkyl.

9. A process comprising hydrogenating nitrile functions present in organic compounds wherein the process utilizes an ionic liquid and at least one heterogeneous catalyst, wherein the anions of the ionic liquid are selected from the group consisting of halides $F^-$, $Cl^-$, $Br^-$, $I_-$, acetate $CH_3COO^-$, trifluoroacetate $CF_3COO^-$, triflate $CF_3SO_3^-$, sulfate $SO_4^{2-}$, hydrogensulfate $HSO_4^-$, methylsulfate $CH_3OSO_3^-$, ethylsulfate $C_2H_5OSO_3^-$, sulfite $SO_3^{2-}$, hydrogensulfite $HSO_3^-$, chloroaluminates $AlCl_4^-$, $Al_2Cl_7^-$, $Al_3Cl_{10}^-$, tetrabromoaluminate $AlBr_4^-$, nitrite $NO_2^-$, nitrate $NO_{3-}$, dichlorocuprate $CuCl_2^-$, phosphates, phosphate $PO_4^{3-}$, hydrogenphosphate $HPO_4^{2-}$, dihydrogenphosphate $H_2PO_4^-$, carbonate $CO_3^{2-}$, hydrogencarbonate $HCO_3^-$, sulfonate —$SO_3^-$, tosylate p-$CH_3C_6H_4SO_3^-$ and bis(trifluoromethylsulfonyl)imide $(CF_3SO_2)_2N^-$ and the ionic liquid contains phosphonium ions and/or at least one five- or six-membered heterocycle which contains at least one phosphorus or nitrogen atom and, optionally, a sulfur and/or oxygen atom.

10. The process according to claim 1, wherein the heterogeneous catalyst comprises a nonpolar surface, and the ionic liquid is a polar ionic liquid.

11. The process according to claim 1, wherein the organic compound and the resulting hydrogenated product reside in a different phase.

12. The process according to claim 1, wherein the heterogeneous catalyst is provided in a fixed bed and the ionic liquid is recirculated in the process.

13. The process according to claim 2, wherein the ionic liquid has a melting point below 200° C.

14. The process according to claim 10, wherein the ionic liquid has a melting point below 200° C.

15. The process according to claim 11, wherein the ionic liquid has a melting point below 200° C.

16. The process according to claim 1, wherein the ionic liquid reversibly coordinates to the catalyst and prevents occupation of the surface of the catalyst by secondary components.

17. The process according to claim 1, wherein the ionic liquid coordinates weakly to the catalyst generating a polar, ionic environment that prevents occupation of the catalyst by secondary components.

* * * * *